United States Patent

Strickland

[11] Patent Number: 5,854,060
[45] Date of Patent: Dec. 29, 1998

[54] DETERMINING BIODEGRADABILITY OF ASPARTIC ACID DERIVATIVES, DEGRADABLE CHELANTS, USES AND COMPOSITIONS

[75] Inventor: Alan D. Strickland, Lake Jackson, Tex.

[73] Assignee: The Dow Chemical Company, Midland, Mich.

[21] Appl. No.: 932,972

[22] Filed: Sep. 18, 1997

Related U.S. Application Data

[62] Division of Ser. No. 607,253, Mar. 4, 1996, Pat. No. 5,776,763, which is a continuation of Ser. No. 281,060, Jul. 27, 1994, abandoned.

[51] Int. Cl.⁶ .............................. C07C 00/00; B09B 3/00
[52] U.S. Cl. ................... 435/262; 435/262.5; 435/263; 435/264; 435/282; 423/DIG. 17
[58] Field of Search ..................... 435/262–264, 435/282; 364/496, 497, 499; 423/DIG. 17

[56] References Cited

U.S. PATENT DOCUMENTS

| 4,855,931 | 8/1989 | Saunders . |
| 5,030,103 | 7/1991 | Buist et al. ............................. 434/278 |

FOREIGN PATENT DOCUMENTS

| 372799 A2 | 6/1990 | European Pat. Off. .......... C08K 5/00 |
| 431189 A1 | 6/1991 | European Pat. Off. ....... G01N 33/00 |
| 506973 A1 | 10/1992 | European Pat. Off. ...... C07C 229/08 |
| WO 86/03971 A1 | 7/1986 | WIPO ............................ A61K 31/70 |
| WO 91/10140 A2 | 7/1991 | WIPO ............................ G01N 33/68 |

OTHER PUBLICATIONS

Lipkowitz et al. ed., *Reviews in Computational Chemistry II*, VCH Publishers, 1991, pp. 313–315.
Lipkowitz et al. ed., *Reviews in Computational Chemistry II*, VCH Publishers, 1991, Chapter 1, pp. 1–47.
Hehre et al., *Experiments in Computational Organic Chemistry*, Wavefunction, Inc., 1993, pp. 47–66.
Lowry et al., *Mechanism and Theory in Organic Chemistry*, Harper and Row, Publishers, 3rd ed., 1987, pp. 69–83.
MOPAC PCMODEL Software, AR Software.
SYBYL Software, Tripos Associates, Inc.
BIOSYM Software, 1993, Tripos Associates, Inc.
HSC Chemistry for Windows, AR Software.
New Chem–X, Chemical Design, Inc.
Kekulé for Macintosh, AR Software.

*Primary Examiner*—David A. Redding

[57] ABSTRACT

Chelants represented by Formula 1b:

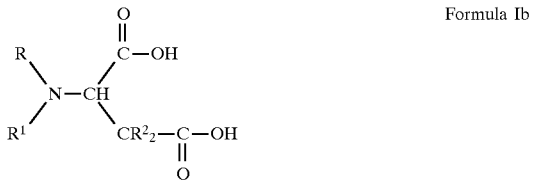

Formula 1b are determined to be biodegradable when Distance A is from about $3.8 \times 10^{-10}$ to about $4.6 \times 10^{-10}$ m, Distance B is from about $5.1 \times 10^{-10}$ to about $5.9 \times 10^{-10}$ m, and Distance C is from about 4.3 to about $6.7 \times 10^{-10}$ m). Compounds meeting these criteria are referred to as compounds of Formula 2. In addition to methods of analysis and computer systems therefor, the invention includes a method of chelating a metal ion to form a chelate and biodegrading the chelate comprising step (a) contacting the metal ion with at least one compound of Formula 2 to form a chelate and (b) contacting the resultant chelate or chelant with microbes of the type specified in ASTM 2667-89, ISO 5815 or effective enzymes thereof under conditions and for a time sufficient for biodegradation wherein either (i) the chelate formed in step (a) is formed in a process of removing deposits, scale, or rust; cleaning or washing; controlling metal initiated or catalyzed oxidation or deterioration including spoilage, discoloration, or rancidification; textile treatment; paper making; stabilization of polymers or phosphates; or petroleum drilling, production or recovery; or (ii) the chelate formed in step (a) is before step (b) used as a redox catalyst, in a process of photographic bleaching, bleach-fixing or developing; in electroless deposition or plating; in removing acid or oxide gases including $H_2S$, $NO_X$, $SO_X$, CO and $CO_2$; or in providing agricultural nutrients.

10 Claims, 3 Drawing Sheets

TWELVE EXAMPLE COMPOUNDS

BIODEGRADABLE

I

II

III

IV

V

VI

NON-BIODEGRADABLE

VII

VIII

IX

X

XI

XII

DETERMINING BIODEGRADABILITY OF ASPARTIC ACID DERIVATIVES, DEGRADABLE CHELANTS, USES AND COMPOSITIONS

This is a divisional of application Ser. No. 08/607,253 filed Mar. 4, 1996 now U.S. Pat. No. 5,776,763, which is a continuation of application Ser. No. 08/281,060 filed Jul. 27, 1994 now abandoned.

This invention relates to determining biodegradability of certain chelants.

Chelants or chelating agents are compounds which form coordinate covalent bonds with a metal ion to form chelates. Chelates are coordination compounds in which a central metal atom is bonded to two or more other atoms in at least one other molecule or ion (called ligand) such that at least one heterocyclic ring is formed with the metal atom as part of each ring.

Chelants are used in a variety of applications including food processing, soaps, detergents, cleaning products, personal care products, pharmaceuticals, pulp and paper processing, water treatment, metalworking and metal plating solutions, textile processing solutions, fertilizers, animal feeds, herbicides, rubber and polymer chemistry, photofinishing, and oil field chemistry. Some of these activities result in chelants entering the environment. For instance, agricultural uses or detergent uses may result in measurable quantities of the chelants being in-water. It is, therefore, desirable that chelants degrade after use.

Biodegradability, that is susceptibility to degradation by microbes, is particularly useful because the microbes are generally naturally present in environments into which the chelants may be introduced. Commonly used chelants like EDTA (ethylenediamine tetraacetic acid) are biodegradable, but at rates somewhat slower and under conditions considered by some to be less than optimum. (See, Tiedje, "Microbial Degradation of Ethylenediaminetetraacetate in Soils and Sediments," Applied Microbiology, Aug. 1975, pp. 327–329.) It would be desirable to have a chelating agent which degrades faster than EDTA or other commonly used chelants.

Biodegradability is determined according to a standardized test such as ASTM D-2667-89. In that test, a standardized sludge containing organisms from a municipal waste treatment plant is used to biodegrade the chelant in the presence of metal ions representative of those found in the environment including iron. Such a test simulates the environment encountered in a municipal waste treatment plant for screening the inherent biodegradability of non-volatile, water-soluble compounds. Biodegradability according to this test is defined as at least about 80 weight percent of a compound biodegraded on a daily basis after an accommodation period of less than or equal to 28 days. In an extension of the procedure, and with the term "onset" used to mean the first day that 80 weight percent of the compound is degraded in 24 hours, a material is considered borderline biodegradable if onset of biodegradation is between days 29 and 49. Materials are not considered biodegradable if onset of biodegradation takes more than 49 days.

It would be desirable to have a more rapid process to determine chelant biodegradability. It would also be desirable for this process to be able to determine borderline biodegradability.

SUMMARY OF THE INVENTION

The invention is an analytical process for determining biodegradability of compounds having a moiety of the formula:

Formula Ia wherein each $R^2$ is independently hydrogen or an unsubstituted or inertly substituted alkyl, aryl, alkaryl, or aralkyl group and wherein the distance between the carboxyl carbon atoms is designated "Distance A", the distance between carboxyl double bonded oxygen atoms is designated "Distance B", and the distance between carboxyl hydroxy groups "Distance C" comprising: determining, in energetically feasible conformations of a compound having a moiety of Formula 1a, whether at least one of (a) Distance A is outside a range of from about $3.81 \times 10^{-10}$ m to about $3.86 \times 10^{-10}$ m;
(b) Distance B is outside a range of from about $5.13 \times 10^{-10}$ m to about $5.52 \times 10^{-10}$ m;
(c) Distance C is outside a range of from about $5.28 \times 10^{-10}$ m to about $6.09 \times 10^{-10}$ m; or
(d) the lowest unoccupied molecular orbital, hereinafter referred to as LUMO, is on at least one atom other than carboxyl carbon atom of the aspartic acid group of Formula 1a. If even one of Distances A, B, and C is outside the given ranges or the LUMO is on other than a carboxyl carbon in the aspartic moiety in each energetically feasible conformation, then the compound is not expected to be biodegradable, but if it is within all the ranges in at least one energetically feasible combination, the compound is expected to be at least borderline biodegradable.

Stated differently, the invention includes a process for determining the biodegradability of compounds having a moiety of the formula:

Formula Ia wherein each of $R^2$ is independently hydrogen or an unsubstituted or inertly substituted alkyl, aryl, alkaryl, or aralkyl group and wherein, the distance between the carboxyl carbon atoms is designated "Distance A", the distance between carboxyl double bonded oxygen atoms is designated "Distance B", and the distance between carboxyl hydroxy groups "Distance C" comprising:

(a) determining Distance A, Distance B And Distance C in at least one energetically feasible conformation;
(b) ascertaining whether distance A is at least about $3.81 \times 10^{-10}$ m but less than or equal to about $3.86 \times 10^{-10}$ meters (m);

(c) ascertaining whether distance B is at least about $5.13 \times 10^{-10}$ m but less than or equal to about $5.52 \times 10^{-10}$ m; and (d) ascertaining whether distance C is at least about $5.28 \times 10^{-10}$ m but less than or equal to about $6.09 \times 10^{-10}$ m; and (e) determining whether the lowest unoccupied molecular orbital, hereinafter referred to as LUMO, is on at least one carboxyl carbon atom of the aspartic acid group. When the criteria represented by Steps (b), (c), (d) and (e) are met, the compound is biodegradable. If, however, even one of the criteria is not met for all energetically feasible conformations, then the compound is not biodegradable. Therefore, it is not necessary that all of (b), (c), (d) and (e) be tested if one or more is not met.

The invention additionally includes a computer system comprising:

(a) means for ascertaining Distance A, Distance B and Distance C in at least one energetically feasible conformation of a compound having a moiety of Formula 1a:

(b) means for determining whether distance A is at least about $3.81 \times 10^{-10}$ m but less than or equal to about $3.86 \times 10^{-10}$ m;

(c) means for determining whether distance B is at least about $5.13 \times 10^{-10}$ m but less than or equal to about $5.52 \times 10^{-10}$ m; and (d) means for determining whether distance C is at least about $5.28 \times 10^{-10}$ m but less than or equal to about $6.09 \times 10^{-10}$ m;

(e) means for determining whether the lowest unoccupied molecular orbital, hereinafter referred to as LUMO, is on at least one carboxyl carbon atom of the aspartic portion of the molecule.

In another aspect the invention is the method of using a compound having a moiety of Formula 1a wherein wherein Distance A is from about 3.81 to about 3.86 Angstroms (Å) (about $3.81 \times 10^{-10}$ to about $3.86 \times 10^{-10}$ m), Distance B is from about 5.13 to about 5.52 Å (about $5.13 \times 10^{-10}$ to about $5.52 \times 10^{-10}$ m), and Distance C is from about 5.28 to about 6.09 Å (about $5.28 \times 10^{-10}$ to about $6.09 \times 10^{-10}$ m) and having its lowest unoccupied molecular orbital, hereinafter referred to as LUMO, on at least one carboxyl carbon atom of the aspartic portion of the molecule (hereinafter referred to as a compound of Formula 2 whether in the acid, salt or chelate form) to chelate metal ions by contacting the ions with the acid or salt form of compounds of Formula 2 and subsequently contacting the resultant chelates, residual chelants or chelants from which the metal is removed with microbes of the type specified for use in ASTM D 2667-89 (both parts) or ISO 5815 (BOD 5 test) or effective enzymes thereof (hereinafter collectively Effective Microbes) under conditions and for a time sufficient for biodegradation wherein either (i) the chelate formed in step (a) is formed in a process of cleaning or washing; removing deposits, scale, or rust; controlling metal initiated or catalyzed oxidation or deterioration including spoilage, discoloration, and rancidification; textile treatment; paper making; stabilization of polymers or phosphates; or petroleum drilling, production or recovery; or (ii) the chelate formed in step (a) is, before step (b), used as a redox catalyst; in a process of photographic bleaching, bleach-fixing or developing; in electroless deposition or plating; in removing acid or oxide gases including $H_2S$, $NO_x$, $SO_x$, CO and $CO_2$; or in providing agricultural nutrients.

In another aspect, the invention is a process of washing comprising contacting an aqueous washing system comprising an organic detergent surfactant selected from the group consisting of anionic detergents, cationic detergents, nonionic detergents, ampholytic detergents, zwitterionic detergents, and mixtures thereof and at least one water-soluble salt of an acid of Formula 2 selected from the group consisting of alkali metal salts, ammonium salts, and alkyl ammonium salts with a material to be washed and subsequently contacting the compound or resultant chelates thereof with Effective Microbes under conditions and for a time sufficient for biodegradation.

In yet another aspect, the invention includes a cleaning process of contacting with a hard surface, a hard surface cleaning composition comprising at least one acid or salt compound of Formula 2 and subsequently contacting the compound or resultant chelates with Effective Microbes under conditions and for a time sufficient for biodegradation.

In another aspect, the invention includes a process of bleaching or bleach-fixing an exposed color photographic material which comprises contacting said material with a bleaching solution or bleach fixing solution containing a bleaching agent comprising a ferric chelate of Formula 2 and subsequently contacting the compound or chelates thereof with Effective Microbes under conditions and for a time sufficient for biodegradation.

The invention also includes a process of electroless plating using various metals, especially copper. It includes a process of electroless deposition of copper upon a non-metallic surface receptive to the deposited copper including a step of contacting the non-metallic surface with an aqueous solution comprising a soluble copper salt and an acid or salt compound of Formula 2 and subsequently contacting the compound or resultant chelates with Effective Microbes under conditions and for a time sufficient for biodegradation. Also included is a process of electroless copper plating which comprises immersing a receptive surface to be plated in an alkaline, autocatalytic copper bath comprising water, a water soluble copper salt, and an acid or salt compound of Formula 2 and subsequently contacting the compound and/or resultant chelates thereof with Effective Microbes under conditions and for a time sufficient for biodegradation.

Additionally, there is an improvement in a process for plating copper on non-metallic surfaces, only selected portions of which have been pretreated for the reception of electroless copper, by immersing the surface in an autocatalytic alkaline aqueous solution comprising, in proportions capable of effecting electroless deposition of copper, a water soluble copper salt, a complexing agent for cupric ion, and a reducing agent for cupric ion, the improvement comprising using as the complexing agent for cupric ion, a salt or acid compound of Formula 2 and subsequently contacting the compound or resultant chelates with Effective Microbes under conditions and for a time sufficient for biodegradation.

Another aspect of the invention includes a process for removing iron oxide deposits from a surface including a step of contacting the deposits with a solution comprising an ammoniated compound of Formula 2 and subsequently contacting the compound or chelates thereof with Effective Microbes under conditions and for a time sufficient for biodegradation.

Yet another aspect of the invention involves gas conditioning. In this aspect the invention includes a process of removing $H_2S$ from a fluid comprising contacting said fluid with an aqueous solution at a pH suitable for removing $H_2S$ wherein said solution contains at least one higher valence polyvalent metal chelate of a compound of Formula 2 and subsequently contacting the compound or chelates thereof with Effective Microbes under conditions and for a time sufficient for biodegradation.

Another aspect of the gas conditioning invention includes a process of removing $NO_X$ from a fluid comprising contacting the fluid with an aqueous solution of at least one lower valence state polyvalent metal chelate of a compound of Formula 2 and subsequently contacting the compound or chelates thereof with Effective Microbes under conditions and for a time sufficient for biodegradation.

DETAILED DESCRIPTION OF THE INVENTION

It has now been found that aspartic acid derivatives of certain molecular geometric conformations in their low energy states are much more probable to exhibit biodegradability than those other conformations. When all molecular criteria are met, the probability of biodegradability or borderline biodegradability is at least about 95 percent, more preferably at least about 98 percent, most preferably at least about 99 percent. The compounds are advantageously biodegradable if other portions of the molecule do not poison microbes involved in biodegradation or Effective Microbes.

Determining biodegradability, therefore, comprises a step of (a) determining molecular distances between the carbonyl carbons hereinafter "Distance A", the double bonded carbonyl oxygen hereinafter "Distance B", and the oxygen, of the carbonyl hydroxyl groups hereinafter "Distance C" of the moiety of Formula 1a:

Formula Ia wherein each $R^2$ is independently selected from hydrogen or unsubstituted or inertly substituted alkyl groups, aryl groups, alkaryl groups, or aralkyl groups. For chelating uses each $R^2$ preferably has a structure which renders the compound having a moiety of Formula 1a soluble and a strong chelant. When each of $R^2$ is alkyl it preferably contains from about 1 to about 15 carbon atoms, more preferably from about 1 to about 10 carbon atoms, most preferably from about 1 to about 6 carbon atoms. Each of $R^2$ is preferably either a hydrogen or methyl group. Such groups are referred to herein as aspartic acid groups.

The term "moiety" is used as understood by those skilled in the art to mean part of a molecule, molecular fragment, or molecular structural fragment.

Compounds having a moiety of Formula 1a are compounds having a structure of Formula 1b wherein R and $R^1$ are any molecular structure.

Formula Ib

Preferably each R and $R^1$ is independently selected from hydrogen or unsubstituted or inertly substituted alkyl groups, aryl groups, alkaryl groups, or aralkyl groups.

Alternatively, R and $R^1$ are joined to form a single or multiple ring structure. For chelating uses each R and $R^1$ preferably has a structure which renders the compound of Formula 1b soluble and a strong chelant. When $R^1$ is alkyl it preferably contains from about 1 to about 15 carbon atoms, more preferably from about 1 to about 10 carbon atoms, most preferably from about 1 to about 6 carbon atoms. When R or $R^1$ is aromatic, alkyl aromatic or aromatic alkyl, it preferably contains from about 5 to about 15 atoms, more preferably from about 5 to about 10 atoms, most preferably from about 6 to about 8 atoms, in each case preferably carbon or nitrogen atoms, more preferably carbon atoms. Examples of such R and $R^1$ include but are not limited to furan, 2-methyl furan, imidazole, 1-methyl imidazole, 4-methyl imidazole, indole, pyrrole, and 2-methyl pyrrole.

By inert substitution is meant substitution which does not undesirably interfere with the chelating ability of the compound. Exemplary of such inert substitution are hydroxyl, carboxyl, sulfonyl, phosphoryl, amino, imido, and amino groups. Optional inert substitution includes additional aspartic acid groups and derivatives thereof. When there is more than one aspartic acid group, the compound is biodegradable if any one aspartic acid group meets the criteria for biodegradability; therefore, each such group should be tested by the analytical process or in the computer system until at least one meets the criteria. The term substitution includes hetero atoms (non-carbon atoms) within carbon chains such as in ether groups, pyridine rings and the like.

Determining the distance between atoms is within the skill in the art. For instance, software with which such determinations are optionally made includes CAChe software commercially available from CAChe Scientific, Inc.; PCMODEL software commercially available from Serena Software; HSC Chemistry for Windows, or PCMODEL software commercially available from AR Software; INSIGHT II, DISCOVER, and LUDI software commercially available from BIOSYM; SYBYL, RECEPTOR, and DISCO software commercially available from Tripos Associates, Inc.; and New Chem-X commercially available from Chemical Design, Inc. Examples of such modeling include those disclosed in U.S. Pat. Nos. 5,187,086; 5,250, 665; 4,859,769; 5,208,152; 4,980.462; 5,202,317; 5,196, 404; 4,781,977, and 5,175,273. Alternatively, X-ray crystallography data can be used to acertain distances. The crystallography data is preferably input to a programmed computer or microprocessor to determine distances. Alternatively, molecular models can be used to determine inert atomic distances when the models are dimensionally correct. Examples of such modeling include those disclosed in U.S. Pat. Nos. 4,877,406; 4,906,122; 4,622,014, and 5,030,103. Because of speed and accuracy, determining by programmed computer or microprocessor is preferred.

It is within the skill in the art that such distances are determined at energetically feasible conformations, preferably the lowest energy conformation. An energetically feasible conformation is a conformation having a heat of formation within about 1.5 KCal (6285 Joule (J)) of the heated formation of the lowest energy conformation. Ascertaining the lowest conformation in the energetically feasible conformation is within the skill in the art as shown by such references as Reviews in Computational Chemistry II, Lickowitz et al. ed., VCH Publishers, 1991, pp. 1–47 and Hehre et al., Experiments in Computational Organic Chemistry, Wavefunction, Inc., 1993, pp. 47–66. Software is advantageously used in calculating these conformations. Software is also advantageous in calculating heats of formation of each conformation and the distances between atoms. The lowest energy conformation and energetically feasible conformations are preferably determined by means known as (a) semiclassical (model), harmonic, or molecular mechanical; (b) semiempirical quantum mechanical; and/or (c) ab initio quantum mechanical methods. These methods are within the skill in the art as shown by *Reviews in Computational Chemistry II*, Lickowitz et al. ed., VCH Publishers, 1991, pp. 313–315.

Determination of the lowest unoccupied molecular orbital (LUMO), that is the unoccupied molecular orbital o; lowest energy, the energy level thereof, and its atomic localization is within the skill in the art as illustrated by Lowry et al., *Mechanism and Theory in Organic Chemistry*, 3rd ed. Harper & Row, 1987, pp 69–83. Such determinations are preferably carried out using a programmed computer with software such as CAChe software commercially available from CAChe Scientific, Inc or GAUSSIAN software commercially available from QCPE or Spartan software commercially available from Wavefunction, Inc.

It has now been found that a compound having a distance A of from about 3.81 to about 3.86 Angstroms (about $3.81 \times 10^{-10}$ to about $3.86 \times 10^{-10}$ m), a distance B of from about 5.13 to about 5.52 Angstroms (about $5.13 \times 10^{-10}$ to about $5.52 \times 10^{-10}$ m) and a distance C from about 5.28 to about 6.09 Angstroms (about $5.58 \times 10^{-10}$ to about $6.09 \times 10^{-10}$ m) in their feasible energy conformations and having its lowest unoccupied molecular orbital, hereinafter referred to as LUMO, on at least one carboxyl carbon atom of the aspartic portion of the molecule can be predicted to be at least borderline biodegradable: that is the onset of biodegradation is within 49 days. Compounds having their feasible conformations outside these ranges are found not to be biodegradable or to have the onset of biodegradation in more than 49 days. Determining whether distances A, B, and C are within these ranges is also preferably done utilizing a programmed digital computer or microprocessor.

The process of the invention is preferably carried out using a programmed digital computer or microprocessor in a computer or computerized system. Such a process is diagrammed schematically in FIG. 1 which includes both optional and essential steps.

Figure 1:
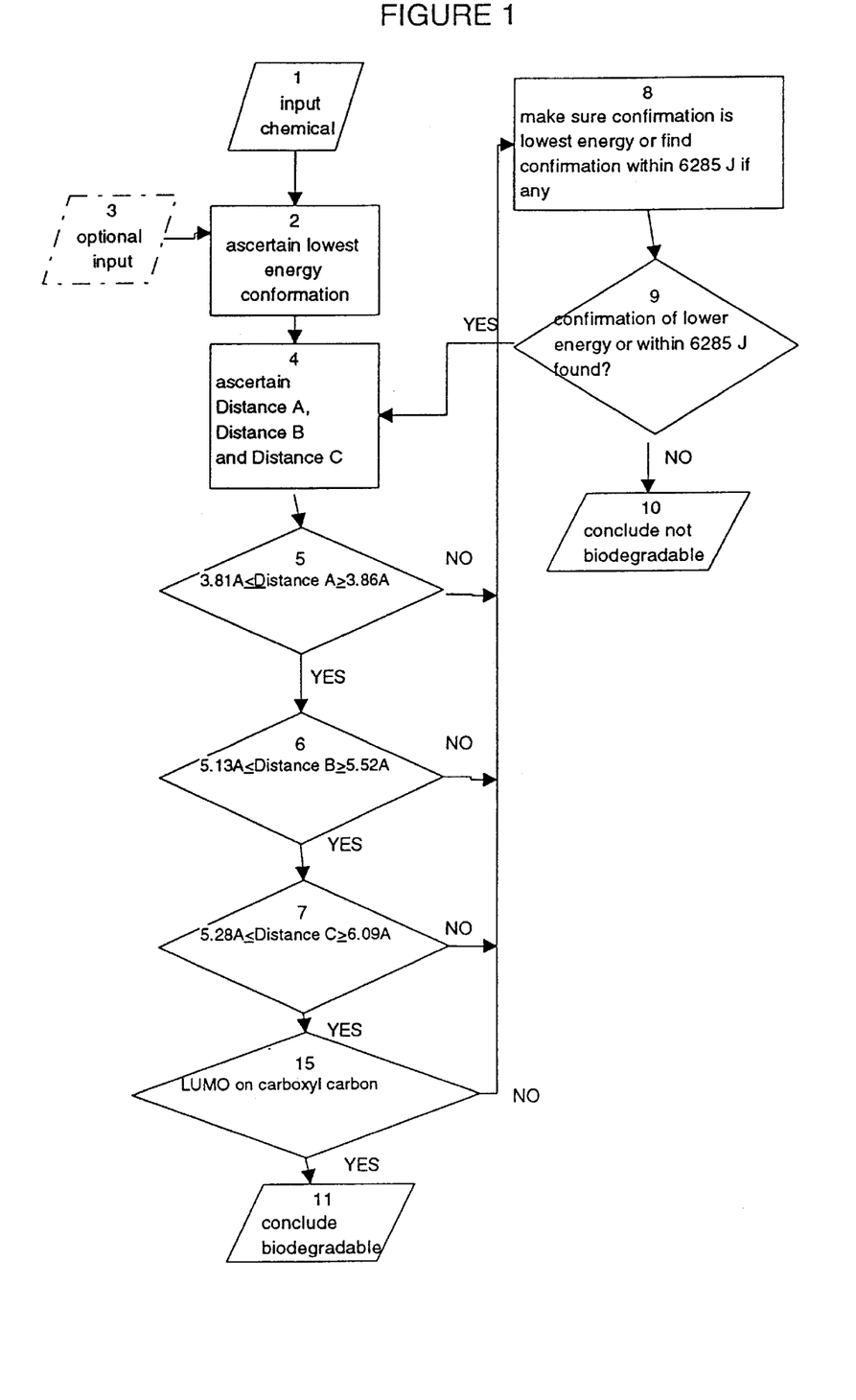
FIG. 1 is a flow chart schematic representation of the process and computer system of the invention.

In Box 1 labeled "chemical input" a chemical is advantageously input into the computer system by a means for input of a chemical within the skill in the art. Such means include input via keyboard, via light pen, via a monitor capable of sensing positions of an input device, via any drawing means such as use of a mouse, graphics pad or tablet. Input from a computer system or software, either the same computer system or a different one is an alternative means of inputting a chemical and is discussed more fully in the discussion of FIG. 2. Alternatively, more than one chemical is input, e.g. for comparison or convenience.

The input chemical is advantageously interpreted into a three dimensional molecular structure and the lowest energy conformation and other low energy conformations are ascertained or determined as represented schematically by Box 2. This determination is within the skill in the art as previously discussed. Optionally there is additional input as represented schematically by Box 3. Box 3, for instance, represents such input as rotation of molecular portions (often referred to in the art as "arms") about other portions such as is used in determining the lowest energy conformation using such software as Sequential Search or Exhaustive Search options of the CAChe software. Optionally, X-ray crystallography data is input. Alternatively, the computer system includes a means for determining low or lowest energy conformations without additional input such as is within the state of the art as represented by such software as MOPAC or PCMODEL software.

Regardless of the various means used to get to this point, Distance A, Distance B and Distance C as previously defined are determined in the essential step represented schematically in Box 4. This determination of distance by a computer system is within the skill in the art as previously discussed.

As schematically represented by Boxes 5, 6 and 7, respectively, it is determined whether Distance A is from about $3.81 \times 10^{-10}$ m to about $3.86 \times 10^{-10}$ m, Distance B is from about $5.13 \times 10^{-10}$ m to about $5.52 \times 10^{-10}$ m, and Distance C is from about $5.58 \times 10^{-10}$ m to about $6.09 \times 10^{-10}$ m. Determining whether numbers representing physical distances are within given ranges is well suited to computer systems and is well within the skill in the art. Determining whether the distances are within the ranges is critical to the practice of the invention. As indicated by FIG. 1, it is not, however, necessary that all the distances be compared with their ranges if one is found to be outside its range.

Box 15 represents a step and corresponding means for determining whether the lowest unoccupied molecular orbital, hereinafter referred to as LUMO, is on at least one carboxyl carbon atom of the aspartic portion of the molecule. Such a determination advantageously includes determination of the LUMO and its atomic localization. Those skilled in the art will recognize that variation in the sequence of such operations is possible; therefore, the operations are represented in a single box.

The sequence of steps represented by Boxes 4, 5, 6, 7 and 15 is not critical in the practice of the invention. For instance, Distance C is optionally ascertained first and determined to be or not be within the given range for Distance C before or after other distances are ascertained or compared with their ranges. An alternative means of accomplishing these steps is to continuously or repetitively compare a distance with the corresponding range as confirmations are explored and not continue exploring any series of molecular conformations, such as, for instance, are obtained by rotation of a molecular fragment or portion which would take any of the distances outside the range. Thus, only confirmations within the ranges would be explored, advantageously except in so far as others might facilitate identifying feasible energy conformations. Similarly the determination of Box 15 is suitably before, after or parallel with that of Boxes 5, 6 and 7.

As is schematically represented by Box 11, molecules having an energetically feasible conformation meeting the criteria of Boxes 5, 6, 7 and 15 would be identified as biodegradable.

When, however, not all the criteria are met, then the computer system preferably has a means for verifying that the conformation measured is, in fact, the lowest energy conformation or an energetically feasible one as schematically represented by optional Box 8. This step is optional because the more readily biodegradable molecules of Formula 1 are identified by their lowest energy conformations having the specified dimensions.

Box 9 schematically represents a determination of whether there are additional energetically feasible conformations. If there are, the steps represented by Boxes 4, 5, 6, 7 and 15 are repeated. If there are not other energetically feasible conformations, then the molecule whose energetically feasible conformations have not met the criteria represented in Boxes 5, 6, 7 and 15 are determined not to be biodegradable within 49 days.

As schematically indicated by Boxes 10 and 11, there is advantageously output indicating whether or not a compound is found to be biodegradable.

Figure 2:
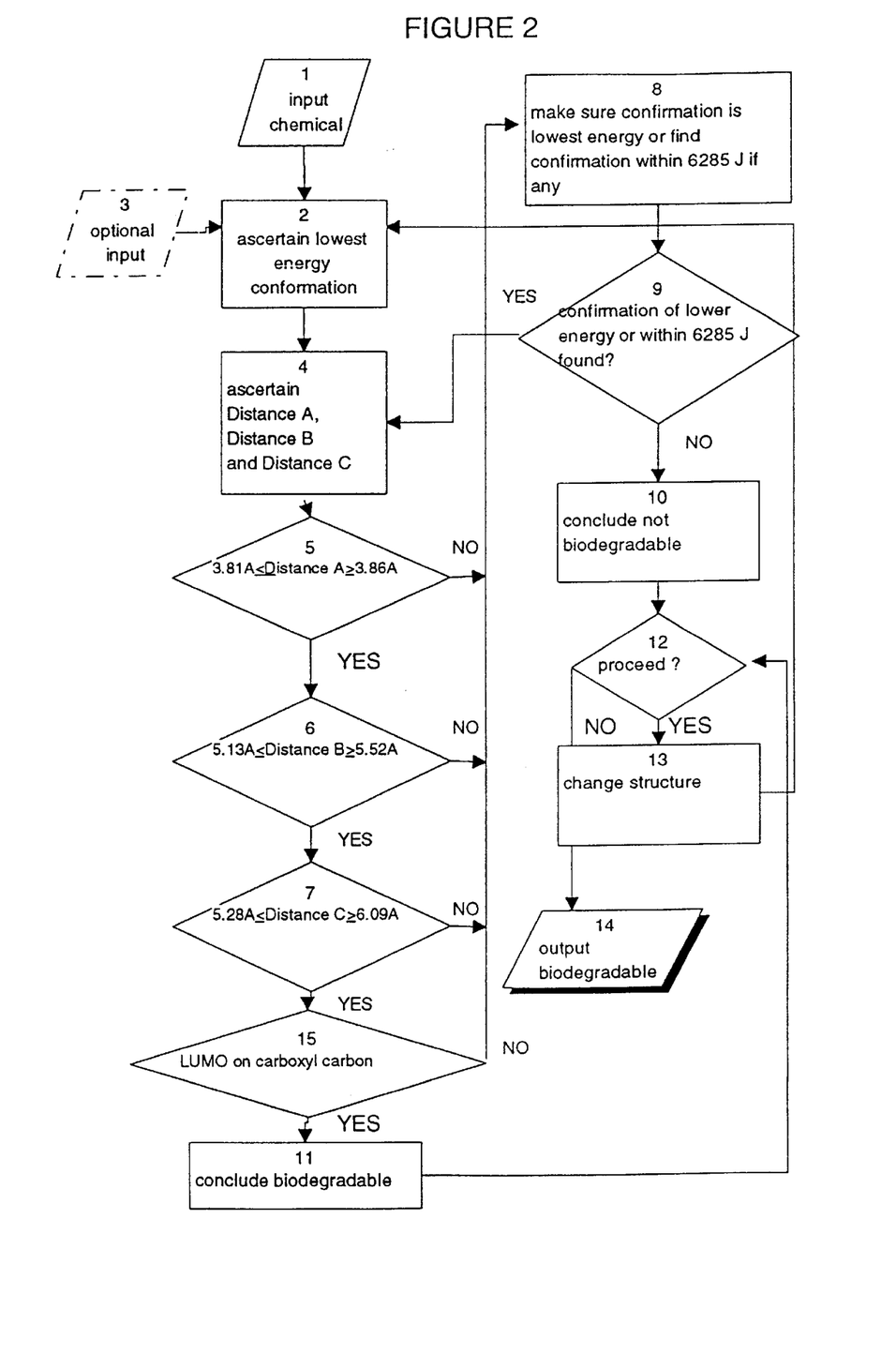
FIG. 2 is a flow chart schematic representation of the process and computer system of the invention with additional optional steps.
Figure 3:
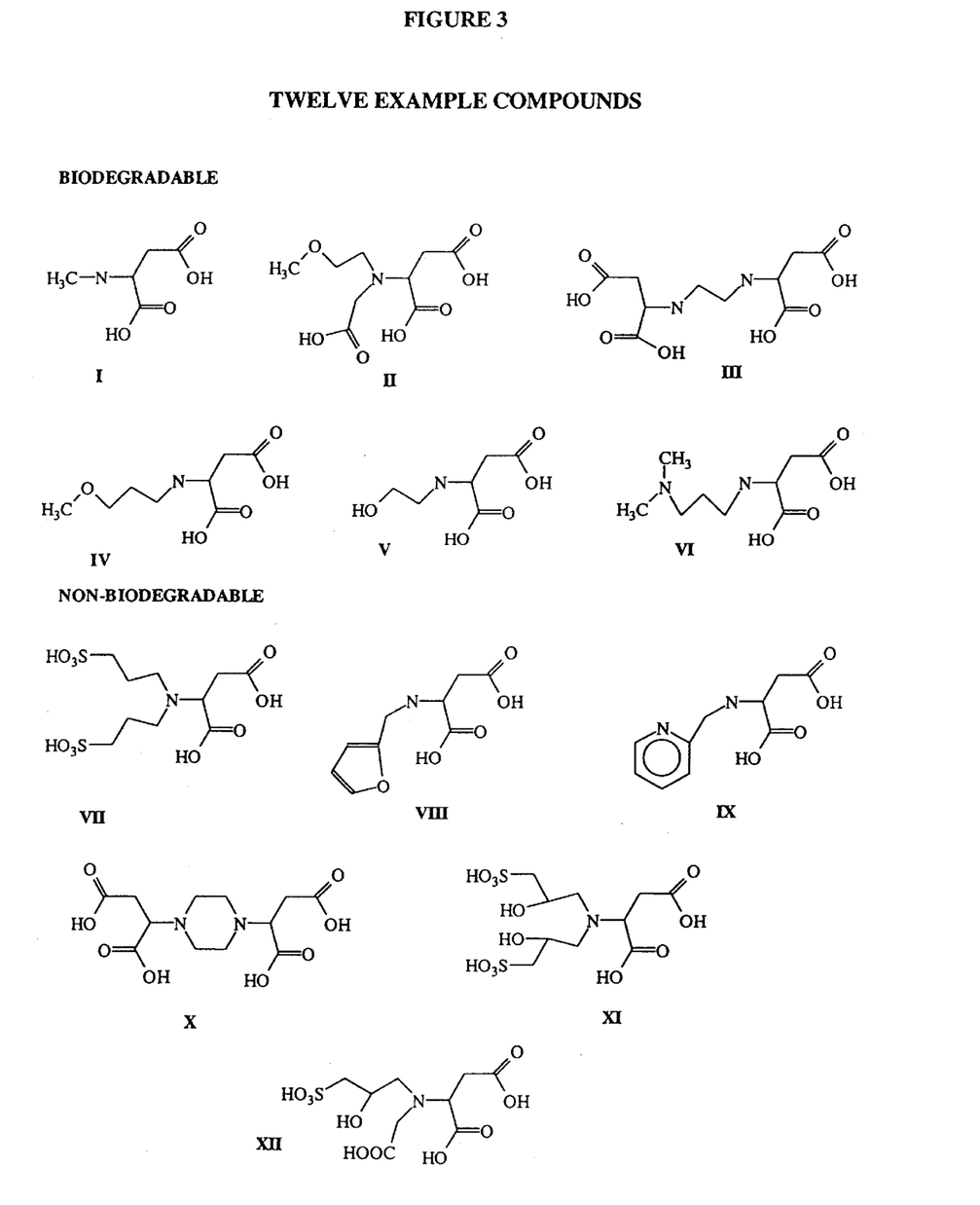
FIG. 3 is a table of the molecular structures considered in the Examples of the Invention.

FIG. 2 illustrates an advantageous variation on the system represented in FIG. 1. More than one chemical structure is considered. The steps and means represented by Boxes 1–11 and 15 are as described for FIG. 1 except that any advantageous output function of Boxes 10 and 11 is advantageously replaced by output represented by Box 14. After a compound is concluded to be biodegradable as represented by Box 11 or to not he biodegradable as represented by Box 10, then the system checks for whether to proceed as represented by Box 12. Box 12 represents a means within the skill in the art, for instance a counter, a check of how many groups have been added to what positions, a check of how many variations have been not biodegradable (e.g. a percentage or a number of consecutive non-biodegradable compounds), a check of the molecular weight or number or ratio of specified atoms, a counter of the time the system has been running or a combination of these.

Optional Box 13, which is executed if the test of Box 12 succeeds, schematically represents a change in the molecular structure from that originally input in Box 1. Such a change is within the skill in the art. For instance, methylene groups, aromatic groups and/or preselected substitutents are successively added at predetermined positions on a molecule. Alternatively, for instance, a predetermined sequence of R groups are considered for the structures of Formula 1. For purposes of this discussion, a change is considered preselected if it is a change in a programmed sequence of changes including, but not limited to, a sequence of molecular structures in a input file or other input sequence. When the changed structure is ascertained or obtained, it goes through the means for ascertaining lowest energy conformation, determination of Distances A, B and C and comparison of those distances with the given ranges represented in Boxes 2–7 and the LUMO measurements and comparisons of Box 15. Alternatively, output from Box 13 goes into input Box 1.

As represented in FIG. 2, when the changes have been made and the means represented by Box 12 indicates not to proceed further in changing the structure, there is output of at least the structures or compounds found to be biodegradable. Advantageously, other compounds considered are also )output with an indication of the findings in each case. Of course, the sequence the output step is not critical. Conveniently, indication of biodegradable compounds is given as they are found, for instance by display means or to printing (including plotting) means.

Thus, the chelants having a moiety of Formula la wherein Distance A is from about 3.81 to about 3.86 Å (about 3.81 to about $3.86 \times 10^{-10}$m), Distance B is from about 5.13 to about 5.52 Å (about 5.13 to about $5.52 \times 10^{-10}$ m) and Distance C is from about 5.28 to about 6.09 Å (about 5.28 to about $6.09 \times 10^{-10}$m) and having their LUMO on at least one carboxyl carbon atom of the aspartic moiety, their salts and chelates are referred to herein as biodegradable chelates or chelants. Compounds having a moiety of Formula 1a having these intraatomic dimensions and placement of LUMO, their salts and chelates are referred to herein as compounds of Formula 2.

Examples of compounds of Formula 2 include
N-methyl aspartic acid
N-carboxymethyl-N-methoxyethyl aspartic acid
N-(N-2-succinyl-2-aminoethyl) aspartic acid
N-(3-methoxypropyl) aspartic acid
N-(2-hydroxyethyl) aspartic acid
N-(N,N-dimethyl-3-aminopropyl) aspartic acid Preparation of compounds of Formula 2 is within the skill in the art, for instance, by processes described by Kezerian et al. in U.S. Pat. No. 3,158,635 which is incorporated herein by reference in its entirety. Kezerian et al disclose, reacting maleic anhydride (or ester or salt) with a polyamine corresponding to the desired polyamino diaspartic acid under alkaline conditions. The reaction yields a number of optical isomers, for example, the reaction of ethylenediamine with maleic anhydride yields a mixture of three optical isomers [R,R], [S,S] and [S,R] ethylenediamine diaspartic acid (EDDS) because there are two asymmetric carbon atoms in ethylenediamine diaspartic acid. These mixtures are used as mixtures or alternatively separated by means within the state of the art to obtain the desired isomer(s). Alternatively, [S,S] isomers are prepared by reaction of such acids as L-aspartic acid with such compounds as 1,2-dibromoethane as described by Neal and Rose, "Stereospecific Ligands and Their Complexes of Ethylenediaminediaspartic Acid", *Inorganic Chemistry*, v. 7. (1968), pp. 2405–2412.

Compounds of Formula 2 are effective as chelants especially for metals such as iron and copper. Effectiveness as a chelant is conveniently measured by titrating the chelant with copper in the presence of an indicator dye, using as an endpoint detector a photosensitive electrode.

The stability constant is conveniently calculated by comparing potentiometric pH measurement of the chelant in the absence of and in the presence of known concentrations of metal ion as described in *Determination and Use of Stability Constants* by Martell and Motekaitis, VCH Publishers, 1985, pp. 14 and 21–27. Various methods may be employed to determine stability constants.

Biodegradable chelants are useful, for instance, in food products vulnerable to metal-catalyzed spoilage or discoloration; in cleaning and laundering products for removing metal ions, e.g. from hard water, that may reduce the effectiveness, appearance, stability, rinsibility, bleaching effectiveness, germicidal effectiveness or other property of the cleaning agents; in personal care products like creams, lotions, deodorants and ointments to avoid metal-catalyzed oxidation and rancidity, turbidity, reduced shelf-life and the like; in pulp and paper processing to enhance or maintain bleaching effectiveness; in pipes, vessels, heat exchangers, evaporators, filters and the like to avoid or remove scaling, in pharmaceuticals; in metal working; in textile preparation, desizing, scouring, bleaching, dyeing and the like; in agriculture as in chelated micronutrients or herbicides; in polymerization or stabilization of polymers; in photography, e.g. in developers or bleaches; in the oil field such as for drilling, production, recovery, hydrogen sulfide abatement and the like. Different metal ions are chelated in the different applications, but for the most part the metals include alkaline earth metals and heavy metals including Fe, Cu, Mn, Zn, Pb, Hg, Ni, Cr, Co, W, Sn, Va, Ti, Ta, Pt, Pd, Zr, Mo, Ca, Mg and Sr.

Advantageous action of biodegradable chelants also includes bleaching agent stabilization, for example for sodium perborate, in detergents and in the bleaching of textiles, pulp or paper stock. Traces of heavy metals, such as iron, copper and manganese, are present in washing compositions themselves, in water and in textile or pulp material, and they catalyze the decomposition of the sodium perborate or other bleaches. The chelants according to the invention bind these metal ions and prevent the undesirable decomposition of the bleaching system during storage and in the wash liquor. This enhances the efficiency of the bleaching system and reduces fiber damage. Such processes are within the skill in the art such as represented by U.S. Pat. Nos. 4,923,941; 4,792,611; 4,822,886, and 4,655,954 which are incorporated herein by reference in their entireties.

In addition, enzymes, optical brighteners and scents are advantageously protected from heavy metal catalyzed oxidative decomposition. Such processes are within the skill in the art such as represented by U.S. Pat. Nos. 4,090,973; 3,954,675; 4,800,037, and 4,529,525 which are incorporated herein by reference in their entireties.

In liquid cleaning formulations the biodegradable chelants can be used as preservatives advantageously in an amount from about 0.05 to about 15 percent by weight, based on the total weight of the formulation. Such processes are within the skill in the art such as represented by U.S. Pat. No. 5,045,580 which is incorporated herein by reference in its entirety.

In soaps the biodegradable chelants prevent, for example, metal catalyzed oxidative decompositions.

Furthermore, they give excellent performance in detergents as builders for preventing precipitates and encrustations on the fabric. Such processes are within the skill in the art such as represented by U.S. Pat. Nos. 5,019,296; 3,629,121; 4,271,032, and 5,082,599 which are incorporated herein by reference in their entireties.

The chelants can be used in industrial processes whenever precipitates of Ca, Mg and other heavy metal and alkaline earth salts are a nuisance and are to be prevented. They are used, for example, for preventing scale deposits and encrustations in kettles, pipelines, spray nozzles or generally on smooth surfaces. Such processes are within the skill in the art such as represented by U.S. Pat. Nos. 4,683,008; 4,606,850; 4,357,254; 4,496,470; 3,460,989, and 4,005,506 which are incorporated herein by reference in their entireties.

They are suitably used for stabilizing phosphates in alkaline degreasing baths and to prevent the precipitation of lime soaps and as a result prevent the tarnishing of Nonferrous surfaces and prolong the service lives of alkaline cleaning baths. Such processes are within the skill in the art such as represented by U.S. Pat. No. 4,395,365 which is incorporated herein by reference in its entirety.

They can be used as chelants in alkaline derusting and descaling baths. The treatment of cooling water with the novel chelants prevents and redissolves scale deposits. Of advantage is the use in an alkaline medium, thereby removing corrosion problems. Such processes are within the skill in the art such as represented by U.S. Pat. Nos. 3,721,629 and 3,959,166 which are incorporated herein by reference in their entireties.

In the polymerization of rubber the chelants are suitably used for preparing e.g. the redox catalysts used therein. They additionally prevent the precipitation of such compounds as iron hydroxide in an alkaline polymerization medium.

In the photographic industry, the chelants are suitably used in developer/fixing baths made up with hard water to alleviate precipitations that lead to fogging on films and photographs and alleviate deposits in the tanks. Iron(III)-complexes of the biodegradable chelants solutions are advantageously used in bleaching and/or bleach fixing baths to bleach silver off exposed color photographic materials. Such processes are within the skill in the art such as represented by U.S. Pat. Nos. 3,893,858; 4,294,914; 4,707,434; and 4,933,266 which are incorporated herein by reference in their entireties.

In the textile industry, the chelants are suitably used for removing heavy metal traces during the manufacture and dyeing of natural and synthetic fibers, thereby preventing many problems, such as dirt spots and stripes on the textile material, loss of luster, poor wettability, unlevelness and off-shade dyeings. Such processes are within the skill in the art such as represented by U.S. Pat. Nos. 4,619,663; 3,539,445, and 4,339,236 which are incorporated herein by reference in their entireties.

In the paper industry, the chelants are suitably used for eliminating heavy metal/iron ions. Iron deposits on paper lead to hot spots where oxidative, catalytic decomposition of the cellulose starts. Such processes are within the skill in the art such as represented by U.S. Pat. Nos. 4,732,650; 4,734,161; 4,938,842; 5,143,580; 5,143,581, and 3,830,690 which are incorporated herein by reference in their entireties.

Exemplary of various other uses are applications in pharmaceuticals, cosmetics and foodstuffs where metal catalyzed oxidation of olefinic double bonds and hence rancidification of goods is prevented. The chelates are also useful as catalysts for organic syntheses (for example air oxidation of paraffins, hydroformylation of olefins to alcohols).

The chelants for alkaline earth metal and heavy metal ions according to the invention reused as complexing agents in general and specifically in detergents and also rinse and wash assistants, in particular as complexing agents for heavy metal and/or alkaline earth metal, ions, as bleaching agent stabilizers and as builders. Such processes are within the skill in the art such as represented by U.S. Pat. Nos. 4,997,587; 4,983,315; 4,906,397; 4,698,181; 4,436,637; 4,439,355, and 4,207,198 which are incorporated herein by reference in their entireties.

Chelants of the invention are also useful in surfactant-free cleaning compositions including built cleaning compositions suitable for hard-surface cleaning, such as certain automatic dishwashing agents and kitchen or bathroom cleaners. Such cleaning compositions generally comprise from about 1 percent to about 99.95 percent, preferably about 90 percent to about 99 weight percent, of a conventional builder and at least about 0.5 weight percent, typically about 0.1 to about 5 weight percent chelant.

The hard surface cleaners preferably include at least one organic solvent with the chelant and, more preferably also contain at least one builder and/or surfactant. The use of builders which are primarily polyphosphates or nitrogenous chelants like NTA with terpenes, benzyl alcohol or butyl carbinol are discussed in European Patent Applications 40,882; 80,749 and 126,545. The use of glycol ether derivatives as solvents are discussed in European Patent Application 105,863 and U.S. Pat. No. 3,591,510 which patents are incorporated herein by reference in their entireties. More recently, it was noted that solvents preferably have a boiling point of at least about 90° C. (See European Patent Applications 317,542 and 513,948 and U.S. Pat. No. 5,202,050 which patents are incorporated herein by reference in their entireties). Use of solvents of at least about 90° C. results in improved soil-release benefits from the chelate-solvent composition, especially in the removal of calcium soap-soil from surfaces such as bathtub surfaces.

Compounds of Formula 2 are also useful in processes for the electroless deposition of metals such as nickel and copper. Electroless plating is the controlled autocatalytic deposition of a continuous film of metal without the assistance of an external supply of electrons such as is described in U.S. Pat. Nos. 3,119,709 (Atkinson) and 3,257,215 (Schneble et al.) which patents are incorporated herein by reference in their entireties. Non-metallic surfaces are pre-treated by means within the skill in the art to make them receptive or autocatalytic for deposition. All or selected portions of a surface are suitably pretreated. Complexing agents are used to chelate a metal being deposited and prevent the metal from being precipitated from solution (i.e. as the hydroxide and the like). Chelating a metal renders the metal available to the reducing agent which converts the metal ions to metallic form.

Such electroless plating is especially useful in the electronics industry, especially for printed circuits.

Metal chelates are important in agriculture because they supply micronutrients (trace metals such as iron, zinc, manganese, and copper) which are vital in the metabolism of both plants and animals. Plant problems previously ascribed to disease and drought are now recognized as possible symptoms of micronutrient deficiencies. Today these deficiencies are generally considered to be caused by (1) the trend toward higher analysis fertilizers containing fewer "impurities"; soils which had been adequately supplied with trace metals from these "impurities" have now become deficient (2) intensified cropping practices which place a severe demand on the soil to supply micronutrients; to maintain high yields, supplementary addition of trace metals is now necessary (3) high phosphorus fertilization, which tends to tie up metals in the soil in a form unavailable to the plant and (4) the leveling of marginal land for cultivation, which often exposes subsoils deficient in micronutrients. The iron, copper, zinc, and manganese chelates of the biodegradable chelants can be used to deliver these metals to the plant. Because of the excellent solubility, these metal chelates are more readily utilized by the plant than are the inorganic forms of the metals. This is especially true in highly competitive ionic systems. As a result, the micronutrients that are chelated to the biodegradable chelants are more efficient than when compared to the inorganic sources. The chelates of iron, manganese, copper, and zinc with the biodegradable chelants are particularly preferred. Biodegradable chelants have less residence time in soil. Such processes are within the skill in the art such as represented by U.S. Pat. Nos. 4,322,361; 4,312,815, and 4,364,871 which are incorporated herein by reference in their entireties.

Further fields of application for the biodegradable chelants include gas washing, conditioning or scrubbing (of e.g. flue, geothermal, sour, synthesis, process, fuel, or hydrocarbon gas) to remove at least one acidic gas, preferably the removal of $NO_X$ from flue gases, $H_2S$ oxidation and metal extraction. Polyvalent-metal chelates of the biodegradable chelants are particularly useful in removing $H_2S$ from a fluid, particularly a gas, containing $H_2S$, by (directly or indirectly) contacting the fluid with at least one chelate of at least one, preferably one polyvalent metal in a higher valence state such that sulfur is formed along with the chelate of the metal in a lower valence state. The chelate of any oxidizing polyvalent metal capable of being reduced by reaction with $H_2S$ or hydrosulfide and/or sulfide ions and, preferably which can be regenerated by oxidation, is suitable. Preferably the chelates are water soluble. Exemplary metals include lead, mercury, nickel, chromium, cobalt, tungsten, tin, vanadium, titanium, tantalum, platinum, palladium, zirconium, molybdenum, preferably iron, copper, or manganese, most preferably iron.

The biodegradable chelants are suitably used in any process of removal of $H_2S$ within the skill in the art such as those exemplified by U.S. Pat. Nos. 4,421,733; 4,614,644; 4,629,608; 4,683,076; 4,696,802; 4,774,071; 4,816,238; and 4,830,838 which are incorporated by reference herein in their entireties. The polyvalent metal chelates are readily formed in aqueous solution by reaction of an appropriate salt, oxide or hydroxide of the polyvalent metal and the chelating agent in the acid form or an alkali metal or ammonium salt thereof.

Similarly, the biodegradable chelants are used in removal of nitrogen oxides, preferably nitric oxide (NO), from fluids containing them. For instance, nitrogen oxides ($NO_X$) and $SO_2$ can be removed from flue gas streams by absorbing the $SO_2$ using an absorbent or reactant therefor, particularly an amine based absorbent such as a nitrogen-containing heterocyclic compound preferably having at least one carbonyl group such as a piperazinone; piperidinone, piperidine, piperazine or triazine having a carbonyl group; hydantoin; cyclic urea, oxazolidone or morpholinone in conjunction with a chelate of a polyvalent metal. Representative metal ions are chromium, cobalt, copper, iron, lead, manganese, mercury, molybdenum, nickel, palladium, platinum, tin, titanium, tungsten, and vanadium; preferably iron, copper, and/or nickel all preferably with a valence of +2, the more preferably iron, most preferably iron in the ferrous state. Such chelates are conveniently prepared by admixing a water soluble salt of the metal, such as a sulfate or acetate with a water soluble form of the chelating agent, e.g. a salt, advantageously in water. The chelates are useful in any process within the skill in the art such as those disclosed in U.S. Pat. Nos. 4,732,744 to Chang et al.; 4,612,175 to Harkness et al.; 4,708,854 to Grinstead; 4,615,780 to Walker; 4,126,529 to DeBerry; 4,820,391 to Walker; and 4,957,716 to Cichanowicz et al. which patents are incorporated herein by reference in their entireties. When an $SO_2$ absorbent is used, it is preferably regenerated, more preferably thermally regenerated, and preferably recycled. The concentration of $NO_X$ in the fluid (directly or indirectly) contacting the chelate is preferably from about 1 ppm to about 15,000 ppm by volume such as is found, for instance, in flue gases from burning e.g. coal.

The newly discovered biodegradability of compounds of Formula 2 renders these processes novel when combined with a biodegradation step. Such a biodegradation step involves contacting compounds of Formula 2 with microbes such as are specified for ASTM 2667-89, ISO 5815 (BOD 5 test) or effective enzymes thereof under conditions and for a time sufficient to result in degradation, preferably of at least about 80 weight percent of the compounds of Formula 2. The time for accommodation is preferably less than or equal to about 49 days more preferably less than or equal to about 35 days, most preferably less than or equal to about 28 days. After accommodation, the compounds of Formula 2 advantageously biodegrade within at least about 24 hours, more preferably at least about 12 hours, most preferably at least about 8 hours. Preferred conditions include contacting compounds of Formula 2, preferably in concentrations below 1 millimolar, with environmentally obtained microbes in an aerated, aqueous solution with an exogenous supply of nutrients for the microbes, more preferably contacting compounds of Formula 2 in concentrations of below 0.1 millimolar with microbes obtained from the activated sludge of a municipal waste treatment plant in an aerated, aqueous solution with intermittent exogenous supply of a portion of the protein and carbohydrate nutrient requirements of the microbes such as is within the skill in the art, for instance as discussed in ASTM 2667-89. The microbes are advantageously environmentally obtained bacteria, preferably environmentally obtained bacteria from aqueous solutions more preferably bacteria obtained from municipal waste treatment plants as activated sludge. The term "environmentally obtained" is used to indicate microbes obtained from soil, water, sewage, public waste water treatment plants, and the like such as is discussed in ASTM 2667-89, especially for the presumptive test. While environmentally obtained microbes are preferred, those skilled in the art will recognize that other microbes, including commercially obtained and bioengineered microbes are suitably used as are enzymes from or acting similarly to the enzymes of any of the microbes. Thus any microbe, enzyme or the like which degrades the compound of Formula 2 is suitably used.

The following examples are offered to illustrate but not limit the invention. Percentages, ratios and parts are by weight unless stated otherwise. Examples of the invention (Ex.) are designated numerically.

EXAMPLE 1

For each of the compounds listed in Tables 1 and 2, molecular modeling is performed using both molecular mechanics and semiempirical techniques. Molecular mechanics is, for example, performed using the augmented MM2 parameter set incorporated in the CAChe software commercially available from CAChe Scientific, Inc. The compound of interest is entered with labeled dihedral angles about the nitrogen-methylene bond of the carboxymethyl arm and the methylene-carbonyl carbon bond for the carboxylic acid arm. This structure is input into the Exhaustive Search procedure. This feature of CAChe creates a "map" of the potential energy surface by setting one of the angles at the first value specified, setting the second angle at its first specified value, optimizing the rest of the molecule, incrementing the second angle by an amount (such as, for example,10 degrees), and repeating the process. The result is a set of optimized conformations for every combination of values of the two angles. Five to twenty of the lowest energy conformations in this map are then optimized with MOPAC using PM3 semiempirical parameters with no restriction on the angles. The energies of these optimized conformations are compared to determine the lowest energy conformation and any other energetically feasible conformations.

Once the optimal conformation for each compound is found, Distance A between the carbonyl carbons, Distance B between the carbonyl oxygen, and Distance C between the hydroxyl oxygen in the aspartic acid portion of the molecule are measured. CAChe software is used to calculate and display molecular orbitals, including specifically the lowest unoccupied molecular orbital (LUMO) for the lowest energy conformations of the molecule. The energies of the orbitals are also calculated.

The measured distances in the lowest energy conformations are listed in Table 2. For each compound, the distances which fall outside the preferred range are underlined and given in bold print. Thus, all of the biodegradable compounds have an energetically favorable conformation which has all three distances within the preferred limits and have the LUMO on an aspartic carboxyl (carbonyl) carbon. All of the non-biodegradable compounds have at least one distance that is outside the range of the preferred limits for the distances and/or have a LUMO on other than an aspartic carboxyl (carbonyl) carbon. None of the non-biodegradable compounds has an energetically feasible conformation with all three distances within the preferred limits and the LUMO on an aspartic carboxyl carbon atom. Table 1 lists the names of the compounds and the number of days until onset of biodegradation as measured by the procedure of ASTM 2667-89, the Semicontinuous Activated Sludge test.

The measured distances in the lowest energy conformations are compared with the limits for each distance, and the localization of the LUMO of the molecule is examined. If the three distance criteria and the criteria for the localization of the LUMO are met, the molecule is found to be biodegradable.

TABLE 1

TWELVE EXAMPLE COMPOUNDS

| | | |
|---|---|---|
| I | N-methyl aspartic acid | 10 |
| II | N-carboxymethyl-N-methoxyethyl aspartic acid | 11 |
| III | N-(N-2-succinyl-2-aminoethyl) aspartic acid [or ethylenediamine disuccinic acid] | 6 |
| IV | N-(3-methoxypropyl) aspartic acid | 11 |
| V | N-(2-hydroxyethyl) aspartic acid | 10 |
| VI | N-(N,N-dimethyl-3-aminopropyl) aspartic acid | 7 |
| VII | N,N-bis(3-sulfonopropyl) aspartic acid | >50 |
| VIII | N-2-furylmethyl aspartic acid | >50 |
| IX | N-2-pyridylmethyl aspartic acid | >50 |
| X | N,N'-bis-(2-succinyl) piperazine [or piperazine disuccinic acid] | >50 |
| XI | N,N-bis-(2-hydroxy-3-sulfonopropyl) aspartic acid | >50 |
| XII | N-carboxymethyl-N-(2-hydroxy-3-sulfonopropyl) aspartic acid | >50 |

TABLE 2

DISTANCES MEASURED FOR EXAMPLE COMPOUNDS

| Compound | C-C | O-O | OH-OH |
|---|---|---|---|
| | Biodegradable | | |
| I | 3.830 | 5.419 | 5.650 |
| II | 3.836 | 5.142 | 6.006 |
| III | 3.825 | 5.28 | 5.837 |
| IV | 3.835 | 5.390 | 5.711 |
| V | 3.859 | 5.176 | 5.850 |
| VI | 3.824 | 5.245 | 5.873 |
| | Nonbiodegradable | | |
| VII | <u>3.163</u> | <u>4.057</u> | <u>5.129</u> |
| VIII | <u>3.111</u> | <u>3.843</u> | <u>5.190</u> |
| IX | 3.837 | 5.346 | 5.797 |
| | <u>3.197</u> | <u>4.031</u> | <u>5.258</u> |
| XI | <u>3.877</u> | 5.386 | <u>5.036</u> |
| XII* | 3.831 | 5.393 | 5.320 |

*These compounds have LUMO on other than an aspartic carboxyl carbon atom.

What is claimed is:

1. A method of chelating a metal ion to form a chelate and biodegrading the chelate comprising step (a) contacting the metal ion with at least one compound having a moiety of the formula Formula Ia wherein each of $R^2$ is independently hydrogen or an unsubstituted or inertly substituted alkyl aryl, alkaryl, or aralkyl group and wherein the distance between the carboxyl carbon atoms is designated "Distance A", the distance between carboxyl double bonded oxygen atoms is designated "Distance B", and the distance between carboxyl hydroxy oxygen groups is designated "Distance C" and wherein Distance A is at least about $3.81 \times 10^{-10}$ m but less than or equal to about $3.86 \times 10^{-10}$ m; Distance B is at least about $5.13 \times 10^{-10}$ m but less than or equal to about $5.52 \times 10^{-10}$ and Distance C is at least about $5.28 \times 10^{-10}$ m but less than or equal to about $6.09 \times 10^{-10}$ m and having the lowest unoccupied molecular orbital, hereinafter referred to as LUMO, is on at least one carboxyl carbon atom of the aspartic acid group, such compounds hereinafter referred to as compounds of Formula 2, to form a chelate and (b) contacting the resultant chelate or chelant with microbes of the type specified in ASTM 2667-89, ISO 5815 or effective enzymes thereof under conditions and for a time sufficient for biodegradation wherein either (i) the chelate formed in step (a) is formed in a process of cleaning or washing; removing deposits, scale, or rust; controlling metal initiated or catalyzed oxidation or deterioration including spoilage, discoloration, or rancidification; textile treatment; paper making; stabilization of polymers or phosphates; or petroleum drilling, production or recovery; or (ii) the chelate formed in step (a) is before step (b) used as a redox catalyst, in a process of photographic bleaching, bleach-fixing or developing; in electroless deposition or plating; in removing acid or oxide gases including $H_2S$, $NO_x$, $SO_x$, $CO$ and $CO_2$; or in providing agricultural nutrients.

2. The method of claim 1 wherein the metal ion is ferric ion and wherein after step (a) and before step (b), the resulting ferric chelate of Formula 2 is used in bleaching or bleach-fixing an exposed color photographic material which includes contacting said material with a bleaching or bleach-fixing solution containing a bleaching agent comprising the ferric chelate.

3. The method of claim 1 wherein the metal ion is copper ion and wherein after step (a) and before step (b), the resulting copper chelate is used in a process of electroless deposition of copper upon a non-metallic surface receptive to the deposited copper including a step of contacting the non-metallic surface with an aqueous solution comprising a soluble copper salt and a compound of Formula 2.

4. The method of claim 1 wherein the metal ion is copper ion and wherein after step (a) and before step (b), the resulting copper chelate is used in a process of electroless copper plating which comprises immersing a receptive surface to be plated in an alkaline, autocatalytic copper bath comprising water, a water soluble copper salt, and a complexing agent which is a compound of Formula 2 for cupric ion.

5. The method of claim 1 wherein step (a) occurs in a process for removing iron oxide deposits from a surface including a step of contacting the deposits with a solution comprising an ammoniated compound of Formula 2.

6. A method of claim 1 wherein step (a) occurs in a process for cleaning a hard surface comprising contacting the surface with a composition of a compound of Formula 2.

7. The method of claim 6 wherein the composition additionally contains an organic solvent having a boiling point of at least about 90° C.

8. The method of claim 1 wherein step (a) occurs in a process for washing articles which comprises contacting the articles with an aqueous washing system consisting essentially of water, an organic detergent surfactant selected from the group consisting of anionic detergents, cationic detergents, nonionic detergents, ampholytic detergents, zwitterionic detergents, and mixtures of such detergents and at least one water-soluble salt of an acid of Formula 2 selected from the group consisting of alkali metal salts, ammonium salts, and alkyl ammonium salts.

9. A method of claim 1 wherein after step (a) and before step (b) the chelate is used in a process of removing $H_2S$ from a fluid comprising contacting said fluid with an aqueous solution at a pH suitable for removing $H_2S$ wherein said solution contains at least one higher valence polyvalent metal chelate of a compound of Formula 2.

10. A method of claim 1 wherein after step (a) and before step (b) the chelate is used in a process of removing $NO_x$ from a fluid comprising contacting the fluid with an aqueous solution of at least one lower valence state polyvalent metal chelate of Formula 2.

* * * * *